United States Patent [19]

Hughes

[11] 4,105,651
[45] Aug. 8, 1978

[54] PURIFICATION OF ENKEPHALIN, AN ENDOGENOUS COMPOSITION IN THE HUMAN BODY AND SYNTHESIS OF SAME

[75] Inventor: John Hughes, Aberdeen, Scotland

[73] Assignee: The United States of America as represented by the Department of Health, Education and Welfare, Washington, D.C.

[21] Appl. No.: 666,647

[22] Filed: Mar. 15, 1976

[51] Int. Cl.² .................... C07C 103/52; A61K 37/00
[52] U.S. Cl. .............................. 260/112.5 R; 424/177
[58] Field of Search ................. 260/112.5 R; 424/177

[56] References Cited

PUBLICATIONS

Hughes et al., Nature, 258, 577–579 (1975).

*Primary Examiner*—Delbert R. Phillips

*Attorney, Agent, or Firm*—John S. Roberts, Jr.; Norman J. Latker; Thomas G. Ferris

[57] ABSTRACT

The purification of an endogenous composition isolated from mammalian brain tissue and termed enkephalin ("in the head"). Enkephalin is recovered from brain tissue by acetone solution and purified by means of column and thin layer chromatography. The composition which is a mixture of two pentapeptides, namely, (a) H-Tyr-Gly-Gly-Phe-Met-OH and (b) H-Tyr-Gly-Gly-Phe-Leu-OH wherein the ratio of a:b is from 3:1 to 4:1 has been found to be a non-addictive narcotic and an opiate agonist.

The synthesis of the pentapeptide composition from the known structure above is accomplished by conventional solution techniques of protection of the amino groups, such as t-butyloxycarbonyl, benzyloxycarbonyl, and t-amyloxycarbonyl, or the solid phase peptide synthesis of R. Bruce Merrifield using a polymeric support and the same or similar amine protecting groups.

5 Claims, No Drawings

PURIFICATION OF ENKEPHALIN, AN ENDOGENOUS COMPOSITION IN THE HUMAN BODY AND SYNTHESIS OF SAME

INTRODUCTION

The present invention involves the purification of an endogenous substance present in mammalian brain tissue which is attracted to pain receptor sites in the brain. Further, this composition acts as an opiate agonist and as such has proved to be a non-addictive narcotic. This substance has been given the name enkephalin (in the mind). The composition of this substance as purified from brain tissue and as synthesized is a combination of two pentapeptides, namely, (a) H-Tyr-Gly-Gly-Phe-Met-OH (methionine-enkephalin) and (b) H-Tyr-Gly-Gly-Phe-Leu-OH (leucine-enkephalin). The present invention is concerned with two facets of enkephalin, namely, (1) its purification and retrieval from brain tissue and (2) the synthesis by known peptide synthesis methods from amino acids in the correct sequence.

The natural enkephalin or endogenous material in laboratory tests has proved at least as potent as morphine of the opiate type drugs. The synthesized variety has also been shown to kill pain after injection into the brains of living rats.

PRIOR ART

Kosterlitz and Hughes, "Some Thoughts on the Significance of Enkephalin, the Endogenous Ligand," *Life Science*, 17:91–96 (1975).

Hughes et al., "Purification and Properties of Enkephalin—the Possible Endogenous Ligand for the Morphine Receptor," *Life Science*, 16:1753–1758 (1975).

Hughes, "Search for the Endogenous Ligand of the Opiate Receptor," *Neurosciences Res. Prog. Bull.*, 13(1):55–58 (1975).

Hughes, "Isolation of an Endogenous Compound from the Brain with Pharmacological Properties Similar to Morphine," *Brain Research*, 88:295–308 (1975).

Hughes et al., "Identification of Two Related Pentapeptides from the Brain with Potent Opiate Agonist Activity," *Nature*, 258:577–579 (1975).

"The Brain's Own Opiate," *Newsweek*, Feb. 23, 1976.

The difference of structure between the present composition, a mixture of two pentapeptides, and the morphine or opiate-type drugs is so different that no direct structure comparison is needed.

GENERAL CONSIDERATIONS

The recovery of enkephalin from its endogenous surroundings in the brain tissue lead finally to the conclusion that from the originally unknown substance the researchers were dealing with, one or more closely related small peptides are readily destroyed by enzymatic action of tissue extracts. In testing the action of enkephalin, it was to be observed that the action of a neurotransmitter or neuromodulator should be rapid, especially in connection with the latter and its relevance to addiction. The tests which were made in the laboratory were of the myenteric plexus-longitudinal muscle of the guinea pig ileum and the vas deferens of the mouse. In the whole animal the rates of onset and recovery are directly related to lipid solubility which facilitates drug movement to and from the brain. It has been found that the rate of onset of the action of enkephalin is at least as fast as that of the most rapidly acting narcotic analgesic, normorphine. The rate of recovery from the action of enkephalin is considerably faster than that of normorphine and it is theorized to be due to its rapid enzymatic degradation.

It is further noted that for an understanding of the phenomena of tolerance and dependence the interaction between endogenous enkephalin and exogenous opiates is of importance. Normally, enkephalin may be assumed to control certain inhibitory mechanisms determining the rate of transmitter release. If, however, opiates are administered with the intent of increasing the effects of these inhibitory mechanisms, e.g., for the purpose of analgesia, then control will pass from the endogenous enkephalin to the exogenous opiates. Since tachyphylaxis is a characteristic of all opiates, a state of tolerance will arise in which increasing amounts of opiate will be required to maintain the inhibitory mechanisms at a level of activity sufficient to prevent signs of withdrawal. Thus, the central nervous system will now be wholly dependent on the concentration of exogenously supplied opiates for the maintenance of essential inhibitory mechanisms.

When the opiates are withdrawn suddenly, these inhibitory mechanisms will become inactive, because any enkephalin which may be available will be unable to stimulate the opiate receptors until they have regained their sensitivity. It may be assumed that the loss of the inhibitory mechanisms normally controlled by enkephalin, will account for many of the symptoms of the withdrawal syndrome. The duration of this syndrome will depend on the rate at which the opiate receptors regain their sensitivity and on the restoration of normal enkephalin synthesis.

PURIFICATION AND PROPERTIES OF ENKEPHALIN

The purification procedure from animal brains (pig brains) of enkephalin is outlined step-wise below:

1. Guinea pig brains were extracted with 5 ml/g acetone. This yielded 0.3–0.5 $\mu$g equivalents per kg of whole brain of dry material.

2. The dry extract was then extracted with methyl alcohol to dissolve enkephalin and precipitate protein and salt. The extract was transferred to aqueous phase and lipids were removed with ether/ethyl acetate at pH 3.

3. A batch absorption was made on Dowex - 50-H$^+$ (styrene-divinylbenzene copolymer — Dow Chemical Co.) at pH 3. The material was washed with 0.1M $NH_4$ acetate pH 5.5 and eluted with 0.2M $NH_4OH$.

4. A batch absorption was made on Amberlite CG400-Formate (bead form exchange resin — Rohm and Haas) at pH 8, washed with 0.1M $NH_4$ formate pH 6.8, eluted with 0.1M formic acid.

5. The freeze dried sample was absorbed on 20 × 1 cm Aminex-A5-$NH_4^+$ column at pH 3 and eluted with 0.3M $NH_4$ formate pH 7.4 at 1 ml/min. Enkephalin emerged over fractions 80–95 ml.

6. The freeze dried sample was dissolved in 1M acetic acid. Gel chromatography was utilized on 100 × 1 cm Sephadex G-15 (bead-formed dextran gel — Pharmacia AB) column with 1M acetic acid. The activity was recovered in fractions 75–90 ml corresponding to a $K_d$ of 1.3.

7. The freeze dried sample was dissolved in 0.07M $NH_4$ formate, injected onto 100 × 0.4 cm AE-SAX Pellionex (Reeve Angel chromatography product) pellicular anion exchange column. Isocratic elution (1 ml/min) with 0.07M $NH_4$ formate in 25% MeOH. Enkephalin mainly eluted in fraction 10-18 ml but with considerable tailing.

8. The freeze dried sample was rechromatographed on 100 × 0.4 cm Sephadex G-15 (bead-formed dextran gel — Pharmacia AB) column with 1M acetic acid.

Discussion

Stages 1-4 above yielded material available for high efficiency liquid chromatography. Complete correspondence between the biological activity and UV absorption at 270 nM was obtained at the final Sephadex G-15 step (8).

Gel chromatography was particularly useful since adsorptive mechanisms as well as gel penetration operated during this separation as evidenced by the high partition coefficient ($K_d$ = 1.3; Step 6) The overall recovery from all the steps averaged 50-55%, the ion exchange steps averaged 85% recovery and the gel filtration 95%. Siliconized glassware was exclusively used in the latter isolation stages. The final freeze dried extract was a white amorphous powder.

The amino acid composition after hydrolysis with 5.5 N HCl at 110° C for 20 hours was: glycine 36.5, methionine 12.3, tyrosine 16.9, phenylalanine 22.5, and leucine 4.2 nmol. Tryptophan was not detected after hydrolysis with 3 N mercaptoethanesulphonic acid at 110° C for 65 hours.

The amino acid sequence was investigated by sequential degradation using the dansyl-Edman procedure [Hartley, Biochem. J., 119:805-822 (1970)]. Molecular weight determinations by electrophoretic mobility indicated a value of approximately 800.

The chain length and sequence assignment at position 5 were resolved by independent mass spectrometric analysis which showed a pentapeptide sequence H-Tyr-Gly-Gly-Phe-Met-OH where methionine is C terminal. Additionally, it was found that the mass spectrum of synthetic H-Tyr-Gly-Gly-Phe-Met-OH as the N-acetyl permethyl derivative has been found to be identical with that of natural enkephalin with the major exception that m/e 622 is absent in the synthetic material. On the other hand, the mass spectrum of the N-acetyl permethyl derivative of synthetic H-Tyr-Gly-Gly-Phe-Leu-OH differs from that of the natural enkephalin mainly by the absence of m/e 640 and the presence of m/e 622 as the most abundant high mass signals. The spectrum of the derivative of a mixture of the two synthetic peptides is identical with that of natural enkephalin. The mass spectrum of natural enkephalin was therefore interpreted as being the result of a mixture of the two pentapeptides H-Tyr-Gly-Gly-Phe-Met-OH (methionine-enkephalin) and H-Tyr-Gly-Gly-Phe-Leu-OH (leucine-enkephalin). It was therefore found that the enkephalin isolated has a ratio of methionine-enkephalin to leucine-enkephalin of 3 or 4 to 1. This conclusion is in agreement with the results of the amino acid analysis.

Both methionine- and leucine-enkephalins have potent agonist activity at opiate receptor sites in that they produce a dose-related inhibition of electrically evoked contractions of the mouse vas deferens and the guinea pig ileum.

PEPTIDE SYNTHESIS

The two synthetic polypeptides H-Tyr-Gly-Gly-Phe-Met-OH (methionine-enkephalin) and H-Tyr-Gly-Gly-Phe-Leu-OH (leucine-enkephalin) were synthesized conventionally using methods described in George R. Pettit, *Synthetic Peptides*, II, Van Nostrand Reinhold, 1971, and solvent systems including counter-current distribution described in Bodanszky and Ondetti, *Peptide Synthesis*, Interscience, 1966, page 185.

In general, the synthesis of peptides depends upon:
(1) the protection of the amino group,
(2) the formation of the peptide linkage, and
(3) the removal of the protecting group.

In the protection of the amino group, a protecting agent such as t-butyloxycarbonyl (BOC) is utilized. A preferred method of analysis which saves time is the so-called solid phase peptide synthesis attributed to R. Bruce Merrifield of the Rockefeller University where the growing peptide is attached chemically to polystyrene beads and as each new unit is added, the reagent and by-product is simply washed away leaving the growing peptide behind ready for another cycle.

Merrifield, in "Solid Phase Peptide Synthesis," *Advances in Immunology*, 32:221-295, 1969, and specially at page 223, defines solid phase peptide synthesis as follows: "Solid phase peptide synthesis is based on the idea that a peptide chain can be assembled in a step-wise manner while it is attached at one end to a solid support. With the growing chain covalently anchored to an insoluble particle at all stages of the synthesis, the peptide will also be completely insoluble and furthermore it will be in a suitable physical form to permit rapid filtration and washing."

An insoluble polymeric support is conventional in the process above termed "the solid phase peptide synthesis" and a preferred polymer is a copolymer of styrene of 2 percent divinylbenzene (DVB) in bead form which has been further modified by chloromethylation. Also utilizable is an insoluble hydroxymethyl resin or polymer.

In actuation the solid support is made to react with the carboxyl group of an amino acid in such a way that the amino acid is bound covalently to the polymer. During this step the amine group of the amino acid is blocked with a protecting group as, for example, with a BOC group (t-butyloxycarbonyl) so that the amine will not react with the polymer. Also utilizable as protecting groups are carbobenzoxy (benzyloxycarbonyl) and t-amyloxycarbonyl.

After removal of this protecting group, a second amino acid can be kept to acylate the exposed amine group of the first amino acid, thus forming the first peptide bond. Historically, the cleavage agent to remove the protecting group is nN NCl in glacial acetic acid. Cf Stewart and Young, *Solid Phase Peptide Synthesis*, Freeman Co., San Francisco, 1969.

EXAMPLE 1

300 g of pig brain tissue was extracted with 80% acetone. The resulting homogenate was filtered and the filtrate evaporated. The residues were then dissolved in 30 ml water. Twenty microliters of this product produced an effect equivalent to a maximal effect of morphine. Small doses of naloxone (60 nM) partially antagonized this action.

In a separate run the mixture was extracted with ethylacetate and ether to remove organic substances and the comparative pharmacological effect compared to morphine was less potent. Sequentially using column chromatography as per Devenyi and Gergely, *Amino Acids, Peptides and Proteins*, Elsevier, 1974, Chapter 8, pages 198-201, and thin layer chromatography using the method of Chapter 9 of Devenyi and Gergely, supra, the substance (enkephalin) was purified to obtain a white powder, later identified as a mixture of the two pentapeptides methionine-enkephalin and leucine-enkephalin. This white powder was hydrophilic and did not dissolve in organic solvents such as acetone, ethyl-acetate, or benzene, but did dissolve in methanol and in water. It was stable toward heating at 80° C for 1 hour, light, and acid conditions. It had a single UV absorption peak at 270 nM.

EXAMPLE 2

Extraction of Tissues

Rabbit, guinea pig, rat and pig brains were studied. The brain was removed as quickly as possible after killing the animal by cervical dislocation, carbon dioxide poisoning or intravenous air embolism. The cortex and cerebellum were discarded and the remainder frozen on solid carbon dioxide and crushed to a fine powder. The powder was stirred for 2 hours with 5 ml/g of acetone containing 0.2 ml of 10 N HCl/liter. The extract was filtered under suction and the solid residues were re-extracted with 5 ml/g of acetone-water (80:20, v/v). The filtrates from the 2 extractions were combined and evaporated down to the aqueous phase under reduced pressure at 28° C. The aqueous extract was centrifuged at 10,000 × g for 30 minutes and the supernatant was collected and taken to dryness under vacuum at 34° C.

The residues remaining after evaporation were redissolved in methane and filtered to remove salts and residual protein. Finally, the methanol was evaporated under vacuum at 34° C and the resulting yellow, waxy residue was stored at −20° C until required. The pH of this extract when dissolved in distilled water was 4.7–5.2.

EXAMPLE 3

Column chromatography

Sephadex G-10 (Pharmacia Fine Chemicals) was swollen overnight in water at 4° C. A glass column 22 × 1 cm was filled with 0.05 M acetic acid and the gel was added as a slurry and allowed to settle under gravity. The columm was equilibrated for 3 hours with 0.05 M acetic acid. Samples (0.2–0.3 ml) were carefully drained into the gel bed after being layered under the acetic acid covering the top of the bed. The column was developed with acetic acid at a flow rate of 0.2 ml/min. The void volume (9.7 ml) of the bed was determined with haemoglobin.

Amberlite CG-120 cation exchange resin (200–400 mesh) was used in the $Na^+$ form and Amberlite CG-400 anion exchange resin (200–400 mesh) in the $Cl^-$ form. Glass columns (8 × 0.5 cm) were slurry packed and the CG-120 and CG-400 resins were equilibrated with 0.1 M sodium acetate pH 4.5 and pH 8, respectively. The ion exchange columns were developed at constant flow rates (0.2–0.4 ml/min).

EXAMPLE 4

Thin layer chromatography

Gelman glass fibre (ITLC-SA) sheets impregnated with silica gel were used. Samples were streaked (100 μl) and after drying the sheet was equilibrated for 1 hour over a mixture of butanol-acetic acid-water (4:1:5) or propan-1-ol-water (95:5). The sheets were developed in the separated butanol phase of the equilibration mixture at 18°–22° C, or in the propan-1-ol solvent. Prior activation of the sheets at 110° C did not alter the observed $R_F$ values. After visualization the sheet was cut into 5 mm strips which were then eluted with 2 ml distilled water and tested for biological activity.

The following detection reagents were sprayed on the sheets for visualization under normal and UV light.
(a) Fluorescamine (Hoffmann-LaRoche) (20 mg/ml acetone) applied after spraying with sodium borate buffer pH 8 or 9
(b) Ninhydrin (0.3 g) in 100 ml n-butanol + 3 ml acetic acid
(c) $K_2Fe_2(CN)_6$ (0.057 g) + $K_2Fe_3(CN_6)$ (0.008 g) in 100 ml water
(d) Sulphuric acid (95%) followed by heating at 110° C
(e) Sulphanilamide (3 g) in 200 ml water + 6 ml HCl (36%) + 14 ml n-butanol. Mixed with $NaNO_2$ (0.3 g) in 20 ml water just before use.
(f) Dragendorff reagent $Bi(NO_3)_3$ (0.85 g) in 10 ml glacial acetic acid and 40 ml water, mixed with equal volume of KI (40%, w/v) in water. One ml of this stock solution was mixed with 2 ml glacial acetic acid and 10 ml water before use.

We claim:
1. A process for recovering and purifying from mammalian brain tissue an endogenous composition having morphine agonist properties consisting of a mixture of two pentapeptides (a) H-Tyr-Gly-Gly-Phe-Met-OH and (b) H-Tyr-Gly-Gly-Phe-Leu-OH wherein the ratio of a:b is from 3:1 to 4:1 and wherein said mammalian brain tissue is extracted with acetone, filtered, transferred to the aqueous phase and separated from lipid impurities by extraction with ether/ethyl acetate at an acid pH of about 3.

2. The process according to claim 1 wherein the ratio of a:b is 3:1.

3. The process according to claim 1 wherein the ratio of a:b is 4:1.

4. The process according to claim 1 wherein the liquid product is purified by chromatography to recover a white powder which displays a single UV absorption peak at 270 nM and an apparent molecular weight by Sephadex exclusion of 300 to 700.

5. A process for recovering and purifying from mammalian brain tissue an endogenous composition having morphine agonist properties consisting of a mixture of two pentapeptides (a) H-Tyr-Gly-Gly-Phe-Met-OH and (b) H-Tyr-Gly-Gly-Phe-Leu-OH wherein the ratio of a:b is from 3:1 to 4:1 wherein said mixture of two pentapeptides is recovered stepwise as follows:
(a) Guinea pig brains are extracted with acetone and the extracts reduced to dryness.
(b) The dry extract is then extracted with methyl alcohol to dissolve the crude endogenous pentapeptide mixture and to precipitate protein and salt. Said methyl alcohol extract is transferred to an aqueous phase and lipids are removed by means of ether/ethyl acetate mixture at pH 3.
(c) A batch absorption of the methyl alcohol extract is made on a styrene-divinylbenzene copolymer $H^+$ at pH 3. The absorption material is washed with 0.1M $NH_4$ acetate pH 5.5 and eluted with 0.2M $NH_4OH$.
(d) A second sequential batch absorption is made on a bead form exchange resin $OH^-$ at pH 8, washed with 0.1M $NH_4$ formate at a pH 6.8, and eluted with 0.1M formic acid and the mixture of the two pentapeptides is recovered.

* * * * *